United States Patent
Kuroda et al.

(10) Patent No.: US 9,885,649 B2
(45) Date of Patent: Feb. 6, 2018

(54) PARTICLE MEASURING APPARATUS AND PARTICLE MEASURING METHOD

(71) Applicant: TOSHIBA MEMORY CORPORATION, Tokyo (JP)

(72) Inventors: Yuichi Kuroda, Mie (JP); Masaki Hirano, Mie (JP); Kenichi Otsuka, Mie (JP)

(73) Assignee: Toshiba Memory Corporation, Tokyo (JP)

( * ) Notice: Subject to any disclaimer, the term of this patent is extended or adjusted under 35 U.S.C. 154(b) by 0 days.

(21) Appl. No.: 15/066,596

(22) Filed: Mar. 10, 2016

(65) Prior Publication Data

US 2017/0074774 A1   Mar. 16, 2017

(30) Foreign Application Priority Data

Sep. 11, 2015   (JP) .................................. 2015-180055

(51) Int. Cl.
*G01N 21/00* (2006.01)
*G01N 15/14* (2006.01)
*G01N 1/22* (2006.01)

(52) U.S. Cl.
CPC ....... *G01N 15/1404* (2013.01); *G01N 1/2205* (2013.01); *G01N 1/2273* (2013.01); *G01N 2001/2255* (2013.01)

(58) Field of Classification Search
CPC .. G01N 21/51; G01N 15/1434; G01N 15/025; G01N 15/1459; G01N 15/0205

USPC .......................................................... 356/338
See application file for complete search history.

(56) References Cited

U.S. PATENT DOCUMENTS

| | | | |
|---|---|---|---|
| 2007/0261740 A1* | 11/2007 | Otsuki ................ | C23C 16/4405 137/561 R |
| 2012/0006675 A1* | 1/2012 | Yamamoto ............ | C23C 14/225 204/192.1 |
| 2012/0258853 A1* | 10/2012 | Veeraraghavan ......... | C09C 1/56 502/62 |
| 2014/0123744 A1* | 5/2014 | Takamiya ............. | G01M 15/10 73/114.75 |
| 2015/0369706 A1* | 12/2015 | Miller .................. | G01N 1/2205 73/863.23 |

FOREIGN PATENT DOCUMENTS

| | | |
|---|---|---|
| JP | 9-304267 | 11/1997 |
| JP | 2005-24409 | 1/2005 |
| JP | 2011-202965 | 10/2011 |

* cited by examiner

*Primary Examiner* — Tarifur Chowdhury
*Assistant Examiner* — Md M Rahman
(74) *Attorney, Agent, or Firm* — Finnegan, Henderson, Farabow, Garrett & Dunner, L.L.P.

(57) ABSTRACT

A particle measuring apparatus according to an embodiment includes a first supply part that introduces first gas. A second supply part introduces second gas having been filtered. A light source irradiates mixture gas including the first gas and the second gas with light. A light detector detects reflected light from the mixture gas and measures number of particles contained in the mixture gas. A pump sucks the mixture gas.

12 Claims, 4 Drawing Sheets

PARTICLE MEASURING APPARATUS AND PARTICLE MEASURING METHOD

CROSS REFERENCE TO RELATED APPLICATIONS

This application is based upon and claims the benefit of priority from the prior Japanese Patent Application No. 2015-180055, filed on Sep. 11, 2015, the entire contents of which are incorporated herein by reference.

FIELD

The embodiments of the present invention relate to a particle measuring apparatus and particle measuring method.

BACKGROUND

In order to measure the number or concentration of particulates (particles) contained in gas, an optical particle measuring apparatus (a particle counter) is often used. The optical particle measuring apparatus measures the number or concentration of particulates by sucking a predetermined amount of atmosphere from a measurement environment and detecting scattered light generated when the sucked atmosphere is irradiated with laser light.

However, if a large amount of gas is required to accurately detect particulates, the state of an environment as a measurement target may be changed. For example, in a case where a particulate concentration in a chamber of a semiconductor manufacturing apparatus is to be measured, a process environment (an atmospheric pressure, for example) in the chamber may be changed if the amount of gas sucked from the chamber is too large. In such a case, the semiconductor manufacturing apparatus cannot manufacture a semiconductor device as designed.

Furthermore, when a high concentration of particulates is contained in a measurement atmosphere, there is a risk that the optical particle measuring apparatus counts a plurality of particulates as one particulate. In such a case, the optical particle measuring apparatus cannot measure the number or concentration of particulates accurately.

DETAILED DESCRIPTION

Embodiments will now be explained with reference to the accompanying drawings. The present invention is not limited to the embodiments.

A particle measuring apparatus according to an embodiment includes a first supply part that introduces first gas. A second supply part introduces second gas having been filtered. A light source irradiates mixture gas including the first gas and the second gas with light. A light detector detects reflected light from the mixture gas and measures number of particles contained in the mixture gas. A pump sucks the mixture gas.

First Embodiment

Figure 1:
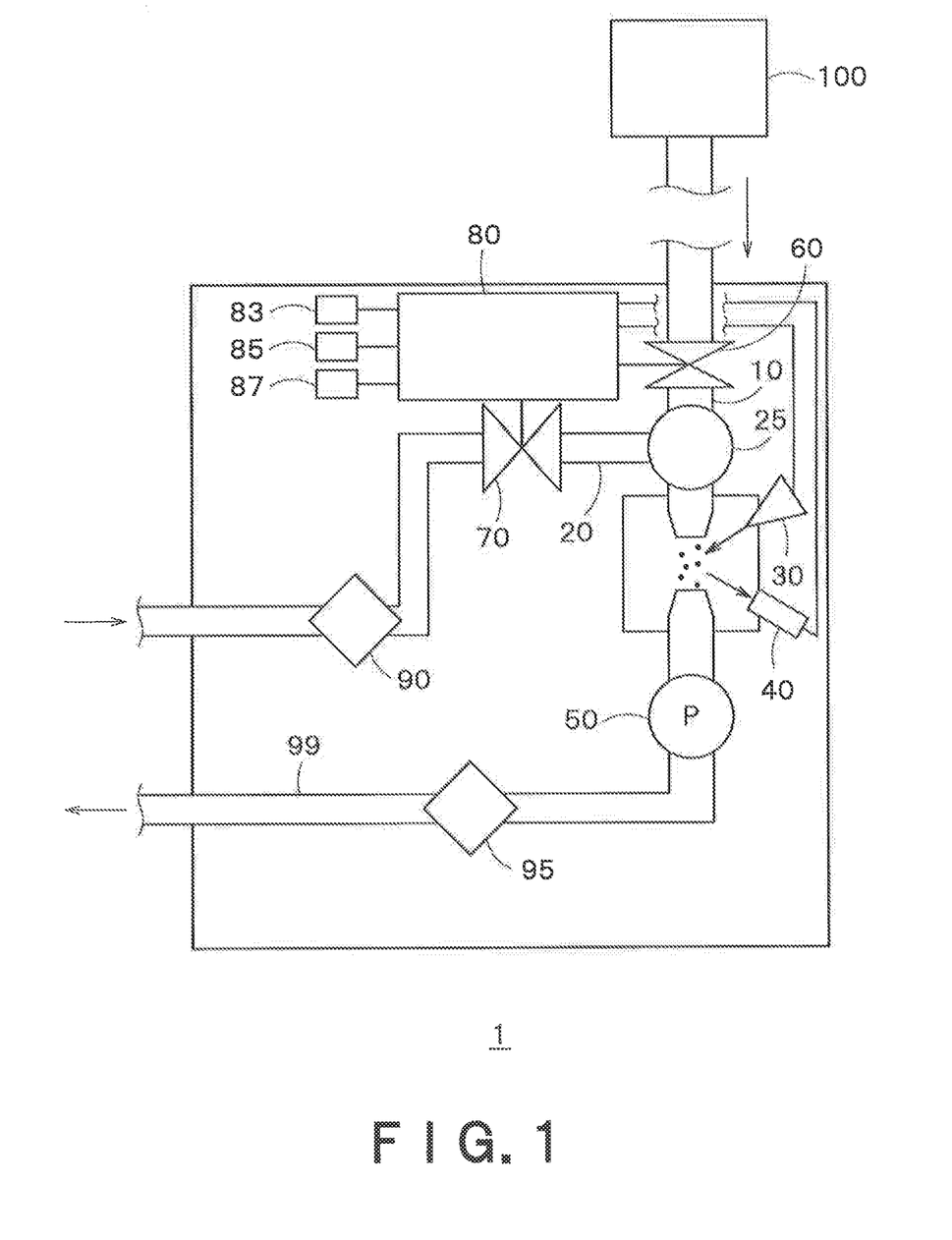
FIG. 1 is a block diagram showing an example of a configuration of a particle measuring apparatus 1 according to a first embodiment.

FIG. 1 is a block diagram showing an example of a configuration of a particle measuring apparatus 1 according to a first embodiment. The particle measuring apparatus 1 includes a first supply part 10, a second supply part 20, an agitator 25, a light source 30, a light detector 40, a pump 50, a first valve 60, a second valve 70, a controller 80, a user interface 83, a storage part 85, a display part 87, filters 90 and 95, and a discharge pipe 99.

The particle measuring apparatus 1 acquires gas from an environment 100 as a measurement target and measures the number or concentration of particles in the gas. That is, the particle measuring apparatus 1 can be a so-called "particle counter". The environment 100 as the measurement target can be, for example, an environment in a clean room to be used in a semiconductor manufacturing process or an environment in a chamber of a semiconductor manufacturing apparatus.

The first supply part 10 is a pipe connecting the environment 100 and the particle measuring apparatus 1 with each other and introduces gas (first gas: hereinafter, also "measurement target gas") in the environment 100 subjected to measurement to the particle measuring apparatus 1. The gas in the environment 100 is sucked by the pump 50 to be introduced from the environment 100 into the first supply part 10. The first supply part 10 transmits the introduced gas to the agitator 25. The measurement target gas can be, for example, air or process gas to be used in a semiconductor manufacturing process.

The second supply part 20 is a pipe having an end connected to the agitator 25 and the other end located outside the particle measuring apparatus 1 and introduces gas outside of the particle measuring apparatus 1 via the filter 90. The outside gas is filtered by the filter 90 and then introduced into the agitator 25. The second supply part 20 can thereby supply cleaned gas (second gas: hereinafter, also "clean gas") obtained by removing particles as impurities from the outside gas to the agitator 25. Alternatively, the second supply part 20 can introduce clean gas from which particles have been already removed from a cylinder or the like. In this case, the filter 90 is not necessarily provided. The clean gas is sucked by the pump 50 to be introduced into the second supply part 20 and supplied to the agitator 25. The clean gas is gas having quite a small number of particles or few particles. The clean gas can be gas of the same kind as that of the measurement target gas or can be gas of a different kind from that of the measurement target gas. For example, when the measurement target gas is hazardous active gas, the clean gas can be safe inert gas different from the measurement target gas.

The agitator 25 is located at a connection portion between the first supply part 10 and the second supply part 20 and agitates and mixes the measurement target gas from the first supply part 10 and the clean gas from the second supply part 20. Mixture gas is thereby generated from the measurement target gas and the clean gas. The mixture gas can be said to be gas obtained by diluting the measurement target gas with the clean gas.

The light source 30 is located downstream of the agitator 25 and irradiates the mixture gas with laser light. When particles in the mixture gas are irradiated with the laser light, the laser light is scattered (reflected) on the particles. A part of the scattered light (reflected light) enters the light detector 40.

The light detector 40 is placed to receive the reflected light from the particles. The light detector 40 detects reflected light from the mixture gas and counts particles contained in the mixture gas. The mixture gas flows according to a suction flow rate of the pump 50 preset as will be described later. Therefore, the controller 80 can calculates the concentration of particles (the density of particles) contained in the mixture gas based on the number of particles measured for a unit time and the amount (the volume) of mixture gas flowing for the unit time.

The pump 50 sucks gas from the first supply part 10, the second supply part 20, and the agitator 25. Suction of gas by the pump 50 introduces the measurement target gas and the clean gas from the first and second supply parts 10 and 20, respectively. In order to accurately measure the number of particles in gas, a certain flow rate of gas is required. Therefore, the pump 50 is designed to suck gas of a flow rate equal to or higher than a given flow rate that is required for measurement of the number of particles. That is, the suction flow rate of the pump 50 is preset at a predetermined flow rate equal to or higher than the given flow rate. The suction flow rate of the pump 50 is stored in the storage part 85 in advance.

The first valve 60 is provided in the first supply part 10 and adjusts the opening degree (the opening area) of the first supply part 10. The first valve 60 thereby adjusts the flow rate of the measurement target gas supplied from the first supply part 10. The flow rate of the measurement target gas is set at such a flow rate (a first flow rate) that does not change a state (the pressure, the gas concentration, or the temperature, for example) of the environment 100. The flow rate of the measurement target gas is registered in advance in the storage part 85 before particle measurement processing.

The second valve 70 is provided in the second supply part 20 and adjusts the opening degree (the opening area) of the second supply part 20. The second valve 70 thereby adjusts the flow rate of the clean gas supplied from the second supply part 20. The flow rate of the clean gas is a flow rate (a second flow rate) obtained by subtracting the flow rate (the first flow rate) of the measurement target gas from the preset suction flow rate of the pump 50. The flow rate of the clean gas will be explained in detail later.

The controller 80 is electrically connected to the light source 30, the light detector 40, and the first and second valves 60 and 70 and controls these units. For example, the controller 80 causes the light source 30 to generate laser light for a predetermined time and obtains the number of particles measured by the optical detector 40 synchronously with the operation of the light source 30. Accordingly, the number of particles in the mixture gas flowing for the predetermined time is known. The concentration of particles (the density of particles) contained in the mixture gas can be calculated based on the amount of the mixture gas flowing for the predetermined time and the number of particles in the mixture gas.

The controller 80 also adjusts the opening degrees of the first and second valves 60 and 70, so that the ratio between the flow rate of the measurement target gas and the flow rate of the clean gas can be adjusted. For example, when the flow rate of the measurement target gas registered in the storage part 85 is lower than the suction flow rate of the pump 50, the controller 80 can supplement the clean gas to set the flow rate of the mixture gas to be substantially equal to the suction flow rate of the pump 50. That is, the controller 80 can change the ratio between the measurement target gas and the clean gas in the mixture gas by controlling the opening degrees of the first and second valves 60 and 70 while setting the flow rate of the mixture gas to be substantially equal to the suction flow rate of the pump 50.

When the opening degrees of the first and second valves 60 and 70 are set, the amount of the measurement target gas and the amount of the clean gas contained in the mixture gas are determined and thus the controller 80 can calculate the concentration of particles in the measurement target gas based on the number of particles contained in the mixture gas and the amount (the volume) of the measurement target gas contained in the mixture gas. In this manner, the controller 80 can calculate the concentration of particles in the measurement target gas.

The user interface 83 is used by an operator to set and input a measurement condition. The user interface 83 can be, for example, a data input device such as a keyboard, a mouse, or a touch screen. The operator inputs, for example, the flow rate of the measurement target gas using the user interface 83. The input flow rate of the measurement target gas is registered in the storage part 85.

The storage part 85 has the preset suction flow rate of the pump 50 stored therein. The suction flow rate of the pump 50 is preset as described above and is registered in the storage part 85, for example, at the time of manufacturing the particle measuring apparatus 1. The storage part 85 also has stored therein the flow rate (the first flow rate) of the measurement target gas input at the time of measurement. The flow rate of the measurement target gas needs to be a level that does not change the state of the environment 100. For example, when the measurement target gas is collected from a chamber of a semiconductor manufacturing apparatus, the flow rate of the measurement target gas needs to be lower than a predetermined flow rate not to change so much process conditions such as the atmospheric pressure, the gas concentration, and the temperature in the chamber. In such a case, the operator sets the flow rate of the measurement target gas at a value lower than the predetermined flow rate and inputs the set value to the user interface 83.

The display part 87 displays a setting condition stored in the storage part 85, the number of particles or the concentration of particles calculated by the controller 80, and the like. The display part 87 can be, for example, a display or a touch screen. The user interface 83 and the display part 87 can be constituted as one touch screen.

The filter 90 is provided in the second supply part 20 to allow gas from outside to pass and generate the clean gas. The filter 90 can generate the clean gas by filtering outside air. The second supply part 20 can alternatively be connected to a cylinder or the like having clean gas and supply the clean gas from the cylinder directly to the agitator 25. In this case, the filter 90 is not necessarily provided. Needless to mention, the second supply part 20 can supply the clean gas from the cylinder further via the filter 90 to the agitator 25. In this case, the filter 90 functions to maintain cleanliness of the clean gas supplied by the second supply part 20.

The discharge pipe 99 is connected to the pump 50 and discharges the mixture gas having passed through the pump 50 to outside the particle measuring apparatus 1. The filter 95 is provided to remove particles from the mixture gas.

An operation of the particle measuring apparatus 1 is explained next.

Figure 2:
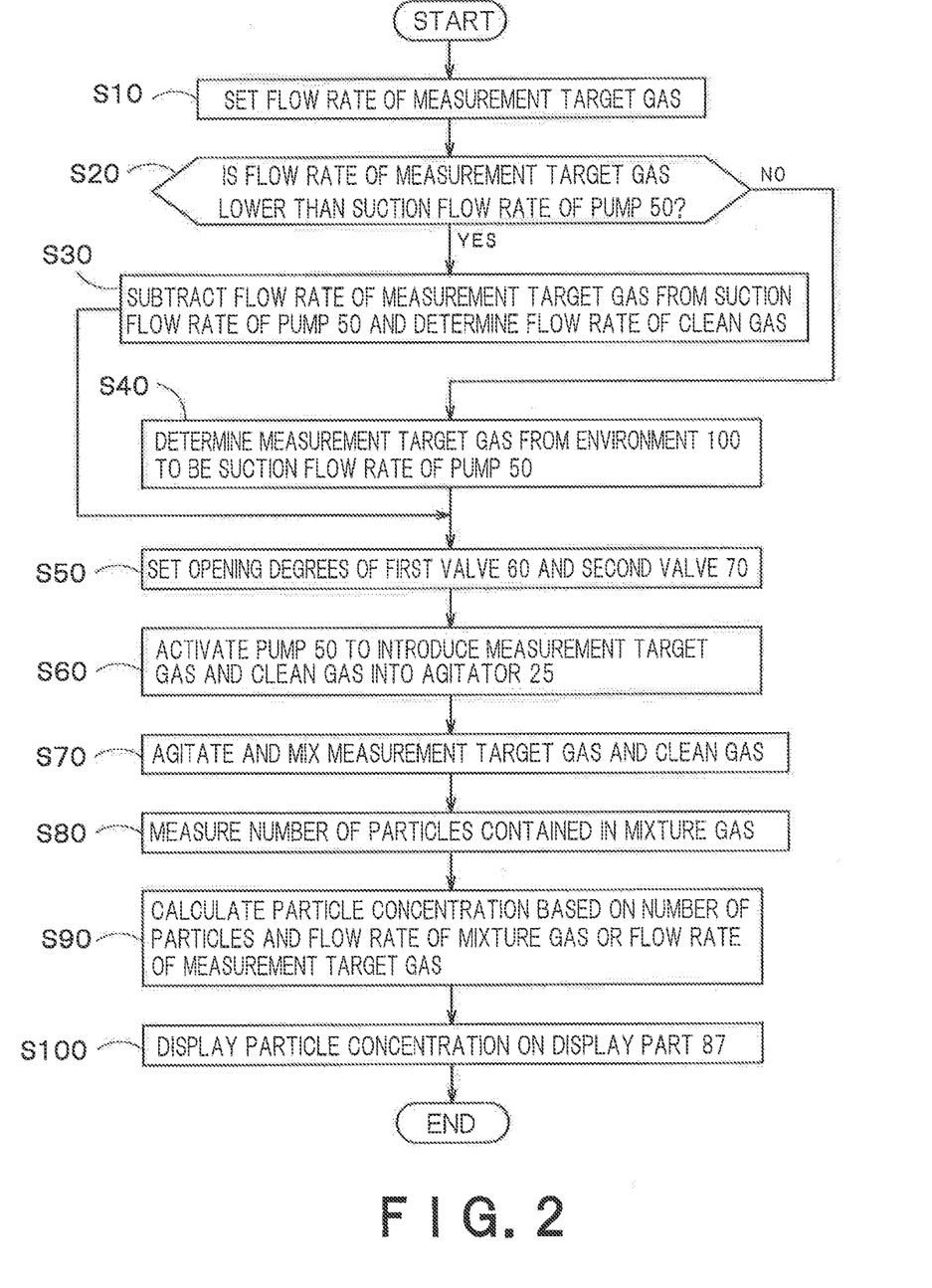
FIG. 2 is a flowchart showing an example of an operation of the particle measuring apparatus 1 according to the first embodiment.

FIG. 2 is a flowchart showing an example of an operation of the particle measuring apparatus 1 according to the first embodiment. The suction flow rate of the pump 50 is preset and already stored in the storage part 85.

First, a flow rate of measurement target gas is set (Step S10). The operator sets the flow rate of the measurement target gas and inputs the flow rate to the user interface 83. The flow rate of the measurement target gas is stored in the storage part 85. As described above, the flow rate of the measurement target gas is set by the operator not to change the state (the pressure, the gas concentration, or the temperature, for example) of the environment 100.

Next, the controller 80 compares the suction flow rate of the pump 50 stored in the storage part 85 and the flow rate of the measurement target gas set at Step S10 with each other (Step S20). When the flow rate of the measurement target gas is lower than the suction flow rate of the pump 50 (YES at Step S20), the controller 80 substrates the flow rate of the measurement target gas from the suction flow rate of the pump 50 and sets a result of the subtraction as the flow rate of the clean gas (Step S30). For example, in an example where the suction flow rate of the pump 50 is set at 30 liters/minute and the flow rate of the measurement target gas is set at 1 liter/minute, the controller 80 determines the flow rate of the clean gas to be 29 liters/minute.

On the other hand, when the flow rate of the measurement target gas is equal to or higher than the suction flow rate of the pump 50 (NO at Step S20), the controller 80 determines the measurement target gas from the environment 100 to be the suction flow rate of the pump 50 without supplementing the clean gas (Step S40). That is, in this case, the flow rate of the measurement target gas becomes substantially equal to the suction flow rate of the pump 50.

Next, the controller 80 sets the opening degrees of the first valve 60 and the second valve 70 (Step S50). At this time, the controller 80 controls the opening degree of the first valve 60 to supply the flow rate of the measurement target gas set at Step S10 from the first supply part 10. The controller 80 also controls the opening degree of the second valve 70 to supply the flow rate of the clean gas calculated at Step S30 from the second supply part 20. For example, when the flow rate of the measurement target gas is lower than the suction flow rate of the pump 50 (YES at Step S20) in the specific example described above, the controller 80 controls the first valve 60 in such a manner that the flow rate of the measurement target gas becomes 1 liter/minute and also controls the second valve 70 in such a manner that the flow rate of the clean gas becomes 29 liters/minute. Accordingly, the measurement target gas of the first flow rate (1 liter/minute, for example) from the first supply part 10 and the clean gas of the second flow rate (29 liters/minute, for example) from the second supply part 20 become mixture gas of a flow rate substantially equal to the suction flow rate (30 liters/minute, for example) of the pump 50. In order to shorten measurement processing, the first valve 60 and the second valve 70 are preferably controlled substantially simultaneously.

In this manner, the controller 80 controls the opening degrees of the first and second valves 60 and 70 to cause the flow rate of the mixture gas to be the suction flow rate of the pump 50. In the first embodiment, the flow rate of the measurement target gas and the suction flow rate of the pump 50 are preset. Therefore, the controller 80 controls the first valve 60 to supply the measurement target gas of the preset flow rate (the first flow rate) and controls the second valve 70 to supply the clean gas of a flow rate (the second flow rate) obtained by subtracting the flow rate of the measurement target gas from the suction flow rate of the pump 50. That is, the controller 80 supplements the clean gas to compensate a shortfall of the flow rate of the measurement target gas relative to the suction flow rate of the pump 50. Assuming that the flow rate of the measurement target gas is F1, the flow rate of the clean gas is F2, and that the suction flow rate is Fp, Expression 1 holds.

$$F2 = Fp - F1 \quad \text{(Expression 1)}$$

As described above, the particle measuring apparatus 1 according to the first embodiment enables the measurement target gas of a lower flow rate to be the mixture gas of a flow rate equal to the suction flow rate of the pump 50 by supplementing the clean gas to the measurement target gas. The particle measuring apparatus 1 can thereby accurately measure the number of particles contained in the measurement target gas.

On the other hand, when the flow rate of the measurement target gas is equal to or higher than the suction flow rate of the pump 50 (NO at Step S20), the controller 80 controls the first valve 60 in such a manner that the flow rate of the measurement target gas becomes 30 liters/minute and also closes the second valve 70 in such a manner that the flow rate of the clean gas becomes zero (not to supply the clean gas). In this case, the mixture gas becomes substantially the measurement target gas.

Subsequently, the pump 50 is activated to introduce the measurement target gas and the clean gas into the agitator 25 (Step S60). The agitator 25 agitates and mixes the measurement target gas from the first supply part 10 and the clean gas from the second supply part 20 (Step S70). Mixture gas generated by the agitator 25 is supplied toward the light source 30 and a measurement position of the light detector 40.

Next, the light source 30 irradiates the mixture gas with laser light and the light detector 40 detects reflected light reflected on particles in the mixture gas. The light detector 40 detects the reflected light and measures the number of particles contained in the mixture gas (Step S80).

Subsequently, the controller 80 calculates the concentration of particles contained in the mixture gas or the measurement target gas based on the number of particles measured by the light detector 40 and the flow rate of the mixture gas or the flow rate of the measurement target gas (Step S90). The particle concentration of the mixture gas can be calculated based on the number of particles measured for a unit time and the amount (the volume) of the mixture gas flowing for the unit time. For example, when the unit time is 1 minute, 30 liters of the mixture gas flow for 1 minute, and n (n is a positive integer) particles are detected in the above specific example, the particle concentration of the mixture gas is n/30 pieces/liter. In this manner, the controller 80 can calculate the concentration of particles contained in the mixture gas based on the measured number of particles and the flow rate of the mixture gas.

Furthermore, the controller 80 can also calculate the concentration of particles in the measurement target gas based on the measured number of particles and the flow rate of the measurement target gas because the flow rate of the measurement target gas is preset. For example, when 1 liter of the measurement target gas flows for a unit time (1 minute) and n particles are detected in the above specific example, the particle concentration of the measurement target gas is n pieces/liter. In this manner, the controller 80 can calculate the concentration of particles contained in the measurement target gas based on the measured number of particles and the flow rate of the measurement target gas.

Next, the controller 80 displays the particle concentration of the mixture gas or the particle concentration of the measurement target gas on the display part 87 (S100). This enables the operator to know the particle concentration of the mixture gas or the particle concentration of the measurement target gas.

Thereafter, the mixture gas used in the measurement is discharged outside the particle measuring apparatus 10 from the discharge pipe 99 through the filter 95.

As described above, the particle measuring apparatus 1 according to the first embodiment includes the second supply part 20 that supplies the filtered clean gas as well as the first supply part 10 that supplies the measurement target gas. Accordingly, even when the flow rate of the measurement target gas is lower than the suction flow rate of the pump 50, the second supply part 20 supplements the clean gas to the measurement target gas, so that the particle measuring apparatus 1 can supply the mixture gas of a flow rate equal to the suction flow rate of the pump 50. The particle measuring apparatus 1 can thereby accurately measure the number of particles contained in the measurement target gas with a reduced flow rate of the measurement target gas collected from the environment 100. A reduced flow rate of the measurement target gas collected from the environment 100 enables the particle concentration of the measurement target gas to be accurately measured without affecting the state of the environment 100. For example, the process environment (such as the atmospheric pressure, the gas concentration, and the temperature) in a chamber of a semiconductor manufacturing apparatus is hardly affected. Accordingly, when the particle measuring apparatus 1 is attached to a semiconductor manufacturing apparatus to measure the particle concentration of measurement target gas, it suffices that the operator sets existing process conditions in the semiconductor manufacturing apparatus and resetting of the process conditions is not required. Furthermore, the semiconductor manufacturing apparatus can manufacture a semiconductor device as designed in the existing process conditions.

When the flow rate of the measurement target gas is set to be lower than the suction flow rate of the pump 50 in a case where the concentration of particles in the measurement target gas is quite high, the second supply part 20 supplements the clean gas to the measurement target gas. The measurement target gas can be thereby diluted with the clean gas. Dilution of the measurement target gas with the clean gas can suppress the light detector 40 from counting a plurality of particulates as one particulate. As a result, even when the concentration of particles in the measurement target gas is quite high, the particle measuring apparatus 1 can accurately measure the number or concentration of the particles in the measurement target gas.

In the first embodiment, the second supply part 20 supplies the clean gas of a flow rate obtained by subtracting the flow rate of the measurement target gas from the suction flow rate of the pump 50. The suction flow rate of the pump 50 is preset and the flow rate of the measurement target gas is set at the time of measurement. Therefore, the controller 80 can automatically determine the flow rate of the clean gas by subtracting the flow rate of the measurement target gas from the suction flow rate of the pump 50 and automatically control the second valve 70 to supply the clean gas of the determined flow rate. As a result, the particle measuring apparatus 1 can automatically adapt the flow rate of the mixture gas including the measurement target gas and the clean gas to the suction flow rate of the pump 50 even when the operator changes the flow rate of the measurement target gas in each measurement.

Furthermore, because the clean gas supplemented to the measurement target gas contains few particles (impurities), it can be considered that the number of particles contained in the mixture gas is substantially equal to the number of particles contained in the measurement target gas. Therefore, the controller 80 can calculate the concentration of particles contained in the measurement target gas based on the number of particles contained in the mixture gas and the flow rate of the measurement target gas. That is, while the particle measuring apparatus 1 according to the first embodiment measures the number of particles in the mixture gas, this is equivalent to measuring the concentration of particles in the measurement target gas. Accordingly, the particle measuring apparatus 1 can calculate the concentration of particles in the measurement target gas as well as the concentration of particles in the mixture gas.

Second Embodiment

Figure 3:
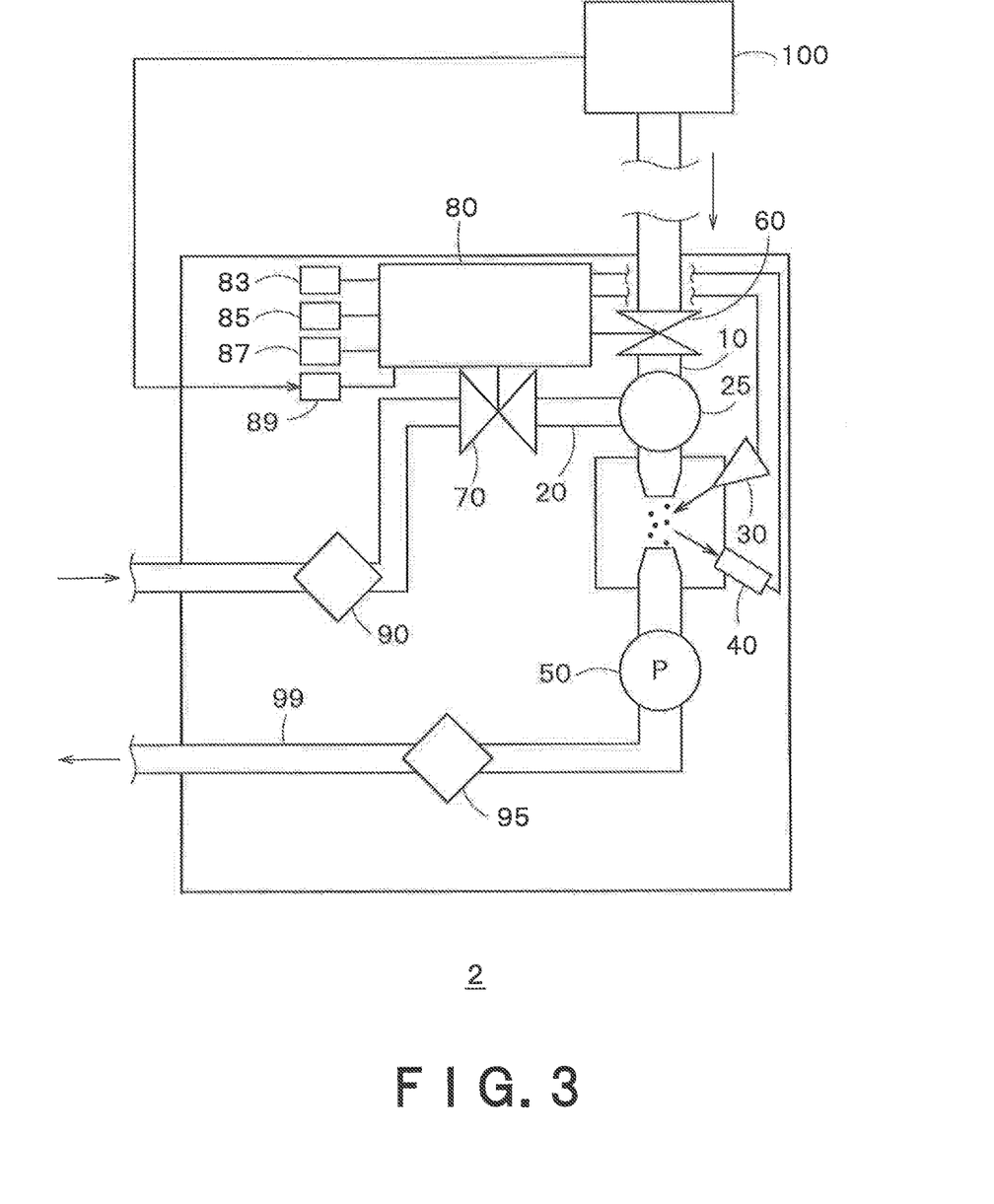
FIG. 3 is a block diagram showing an example of a configuration of a particle measuring apparatus 2 according to a second embodiment.

FIG. 3 is a block diagram showing an example of a configuration of a particle measuring apparatus 2 according to a second embodiment. The particle measuring apparatus 2 further includes an input part 89. The input part 89 receives a measurement value of a parameter in the environment 100 as a target of measurement. The parameter in the environment 100 can be, for example, an atmospheric pressure, a gas concentration, or a temperature in a chamber of a semiconductor manufacturing apparatus. The input part 89 is connected, for example, to a pressure sensor (not shown) provided in a semiconductor manufacturing apparatus and receives a measurement value of the atmospheric pressure in a chamber from the pressure sensor. Alternatively, the input part 89 is connected, for example, to a concentration sensor (not shown) provided in a semiconductor manufacturing apparatus and receives a measurement value of the gas concentration in a chamber from the concentration sensor. Alternatively, the input part 89 is connected, for example, to a thermometer (not shown) provided in a semiconductor manufacturing apparatus and receives a measurement value of the temperature in a chamber from the thermometer. In the second embodiment, the input part 89 is connected online to a device as a target of measurement. However, the measurement value of a parameter in the environment 100 can be measured by the operator and manually input by the operator to the input part 89 or the user interface 83.

The storage part 85 has the parameter measurement value received by the input part 89 stored therein. The storage part 85 also has a parameter setting condition stored therein. The parameter setting condition is, for example, an acceptable range of the atmospheric pressure in a chamber, an acceptable range of the gas concentration therein, an acceptable range of the temperature therein, or the like in the process conditions. Other configurations of the second embodiment can be identical to corresponding ones of the first embodiment.

When the measurement value of a parameter meets such a setting condition of the parameter, the particle measuring apparatus 2 can measure the particle concentration of the measurement target gas while suppressing changes in the state of the environment 100. However, when the measurement value of the parameter deviates from the setting condition of the parameter, it is undesirable that the particle measuring apparatus 2 measures the particle concentration of the measurement target gas because the state of the environment 100 may be greatly changed.

Figure 4:
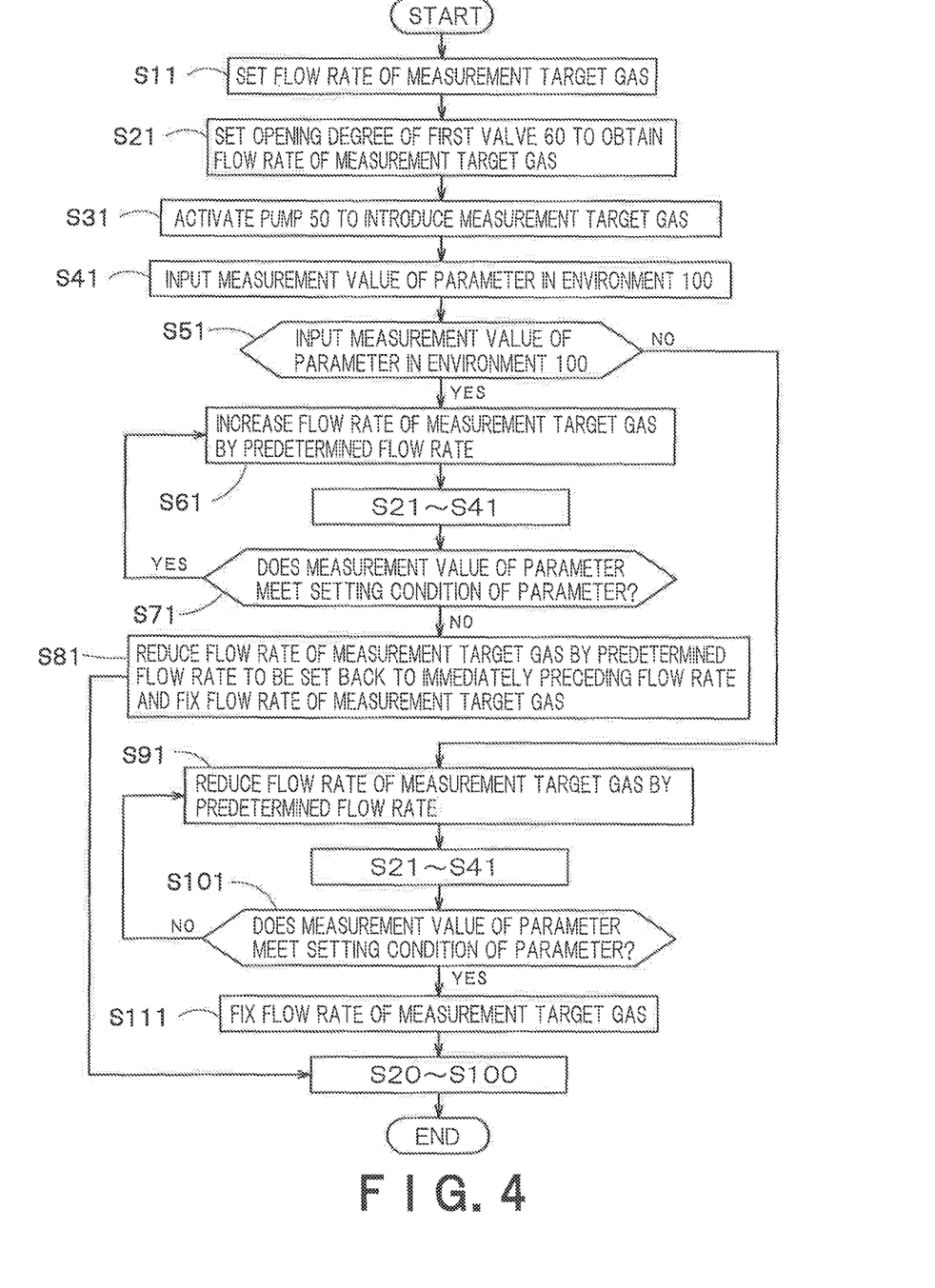
FIG. 4 is a flowchart showing an example of an operation of the particle measuring apparatus 2 according to the second embodiment.

In the second embodiment, the controller 80 therefore controls the first valve 60 in such a manner that the flow rate of the measurement target gas becomes substantially the maximum level while adapting the measurement value of the parameter to the setting condition of the parameter. That is, in the second embodiment, the opening degree of the first valve 60 is automatically set by the controller 80 without set by the operator. For example, FIG. 4 is a flowchart showing an example of an operation of the particle measuring apparatus 2 according to the second embodiment. A setting method of the flow rate of the measurement target gas is explained in more detail with reference to FIG. 4. The suction flow rate of the pump 50 is preset and already stored in the storage part 85.

First, the setting condition of a parameter and the flow rate of measurement target gas are set (Step S11). The setting condition of the parameter is, for example, an acceptable range of the atmospheric pressure in a chamber, an acceptable range of the gas concentration therein, or an acceptable range of the temperature therein in process conditions as described above. It suffices that the setting condition of the parameter is set by the operator and input to the user interface 83. Also the flow rate of the measurement target gas is set by the operator and input to the user interface 83. At this time, it is preferable that the operator set the flow rate of the measurement target gas to a relatively small value to be reliably adapted to the setting condition of the parameter. The flow rate of the measurement target gas is stored in the storage part 85.

Next, the controller 80 sets the opening degree of the first valve 60 to obtain the flow rate of the measurement target gas (Step S21). At this time, the controller 80 controls the opening degree of the first valve 60 to supply the flow rate of the measurement target gas set at Step S11 from the first supply part 10.

Subsequently, the pump 50 is activated to introduce the measurement target gas (S31). At this time, the second valve 70 can be in a closed state.

Next, the input part 89 inputs a measurement value of the parameter in the environment 100 (Step S41). For example, the input part 89 receives a measurement value of the atmospheric pressure in a chamber from a pressure sensor provided in a semiconductor manufacturing apparatus. Alternatively, the input part 89 receives a measurement value of the gas concentration in a chamber from a concentration sensor provided in a semiconductor manufacturing apparatus. Alternatively, the input part 89 receives a measurement value of the temperature in a chamber from a thermometer provided in a semiconductor manufacturing apparatus. The input part 89 can receive the measurement value of the parameter directly from a semiconductor manufacturing apparatus. Alternatively, the operator can input the measurement value of the parameter to the input part 89.

Next, the controller 80 determines whether the measurement value of the parameter input at Step S41 meets the setting condition of the parameter (Step S51). Because the flow rate of the measurement target gas is initially set to a relatively small value, the measurement value of the parameter is considered to meet the setting condition of the parameter.

When the initial measurement value of the parameter meets the setting condition of the parameter (YES at Step S51), the controller 80 increases the flow rate of the measurement target gas by a predetermined flow rate (Step S61). Subsequently, the processes at Steps S21 to S41 described above are performed again. The controller 80 further performs a comparison between a measurement value of the parameter and the setting condition of the parameter (Step S71). When the measurement value of the parameter meets the setting condition of the parameter (YES at Step S71), the processes at Steps S61, S21 to S41, and S71 are repeated.

When the processes at Steps S61, S21 to S41, and S71 are repeated, the flow rate of the measurement target gas gradually increases. When a measurement value of the parameter thereby fails to meet the setting condition of the parameter (NO at Step S71), a measurement value of the parameter at the immediately preceding flow rate of the measurement target gas is supposed to meet the setting condition of the parameter. Therefore, when the flow rate of the measurement target gas is gradually increased by the predetermined flow rate and thereafter a measurement value of the parameter fails to meet the setting condition of the parameter (NO at Step S71), the controller 80 reduces the flow rate of the measurement target gas by the predetermined flow rate to be set back to the immediately preceding flow rate and fixes the flow rate of the measurement target gas to the immediately preceding flow rate (Step S81).

On the other hand, when the initial measurement value of the parameter does not meet the setting condition of the parameter (NO at Step S51), the controller 80 reduces the flow rate of the measurement target gas by the predetermined flow rate (Step S91). Subsequently, the processes at Steps S21 to S41 described above are performed again. The controller 80 further performs a comparison between a measurement value of the parameter and the setting condition of the parameter (Step S101). When the measurement value of the parameter does not meet the setting condition of the parameter (NO at Step S101), the processes at Steps S91, S21 to S41, and S101 are repeated.

When the processes at Step S91, S21 to S41, and S101 are repeated, the flow rate of the measurement target gas gradually reduces. When a measurement value of the parameter thereby turns out to meet the setting condition of the parameter (YES at Step S101), this means that the measurement value of the parameter at a flow rate of the measurement target gas at this time meets the setting condition of the parameter. Therefore, when the flow rate of the measurement target gas is gradually reduced by the predetermined flow rate and thereafter a measurement value of the parameter meets the setting condition of the parameter (YES at Step S101), the controller 80 fixes the flow rate of the measurement target gas to the flow rate at this time (Step S111).

Thereafter, the processes at Steps S20 to S100 in FIG. 2 are performed, so that the particle measuring apparatus 2 can measure the particle concentration of the measurement target gas.

As described above, according to the second embodiment, the particle measuring apparatus 2 can set the flow rate of the measurement target gas to substantially the maximum value while adapting the measurement value of a parameter to the setting condition of the parameter. The flow rate of the measurement target gas can be automatically set to substantially the maximum value while the measurement value of a parameter is adapted to the setting condition of the parameter (changes in the state of the environment 100 are suppressed). Furthermore, according to the second embodiment, the particle measuring apparatus 2 can automatically set the flow rate of the measurement target gas and the flow rate of the clean gas according to the state of the environment 100. This configuration can shorten the measurement time of the particle concentration. In addition, the second embodiment can achieve effects identical to those of the first embodiment.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A particle measuring apparatus comprising:
a first supply part introducing first gas containing particles;
a second supply part introducing second gas having been filtered;
a light source irradiating mixture gas including the first gas and the second gas with light;
a light detector detecting reflected light from the mixture gas and measuring number of the particles contained in the mixture gas;
a pump sucking the mixture gas;
a first valve located in the first supply part;
a second valve located in the second supply part;
a storage part storing a preset first flow rate of the first gas and a suction flow rate of the mixture gas to be sucked by the pump; and
a controller controlling the first valve to supply the first gas of the first flow rate and controlling the second valve to supply the second gas of a second flow rate obtained by subtracting the first flow rate from the suction flow rate,
wherein
the controller controls the second valve to supply the second gas of the second flow rate when the first flow rate is lower than the suction flow rate, and
the controller closes the second valve not to supply the second gas when the first flow rate is equal to or higher than the suction flow rate.

2. The apparatus of claim 1, further comprising an agitator connected between the first supply part and the second supply part and mixing the second gas with the first gas to obtain the mixture gas.

3. The apparatus of claim 1, further comprising a filter located in the second supply part and filtering gas from outside to generate the second gas.

4. The apparatus of claim 1, wherein the controller calculates a concentration of particles contained in the first gas based on number of particles and the first flow rate, the number of particles being measured by the light detector.

5. The apparatus of claim 1, wherein the controller controls the first and second valves substantially simultaneously.

6. The apparatus of claim 1, further comprising an input part inputting a measurement value of a parameter in an environment as a measurement target, wherein
the storage part storing a preset setting condition of the parameter,
the controller controls the first valve to increase the first flow rate of the first gas by a predetermined flow rate when a measurement value of the parameter meets the setting condition of the parameter, and
the controller controls the first valve to reduce the first flow rate of the first gas by the predetermined flow rate and fix the reduced first flow rate when a measurement value of the parameter fails to meet the setting condition of the parameter after the first flow rate of the first gas has been increased by the predetermined flow rate.

7. The apparatus of claim 1, further comprising an input part inputting a measurement value of a parameter in an environment as a measurement target, wherein
the storage part storing a preset setting condition of the parameter,
the controller controls the first valve to reduce the first flow rate of the first gas by a predetermined flow rate when a measurement value of the parameter does not meet the setting condition of the parameter, and
the controller fixes the first flow rate of the first gas when a measurement value of the parameter meets the setting condition of the parameter after the first flow rate of the first gas has been reduced by the predetermined flow rate.

8. The apparatus of claim 1, wherein a display part displays number of particles contained in the mixture gas or a concentration of particles contained in the first gas.

9. A particle measuring method using a particle measuring apparatus comprising a first supply part introducing first gas containing particles, a second supply part introducing second gas having been filtered, a light source irradiating mixture gas including the first gas and the second gas with light, a light detector detecting reflected light from the mixture gas and measuring number of the particles contained in the mixture gas, and a pump sucking the mixture gas,
the method comprising:
calculating a second flow rate of the second gas by subtracting a first flow rate of the first gas from a suction flow rate of the mixture gas sucked by the pump;
generating mixture gas by mixing the first gas of the first flow rate and the second gas of the second flow rate;
irradiating the mixture gas with light;
detecting reflected light from the mixture gas and measuring number of the particles contained in the mixture gas; and
calculating a concentration of particles contained in the first gas based on the measured number of particles and the first flow rate,
wherein
the particle measuring apparatus further comprises a first valve located in the first supply part, a second valve located in the second supply part, and a controller controlling the first and second valves,
the controller controls the first valve to supply the first gas of the first flow rate and controls the second valve to supply the second gas of the second flow rate,
the controller controls the second valve to supply the second gas of the second flow rate when the first flow rate is lower than the suction flow rate, and
the controller closes the second valve not to supply the second gas when the first flow rate is equal to or higher than the suction flow rate.

10. The method of claim 9, wherein
the first flow rate of the first gas is set by:
inputting a measurement value of a parameter in an environment as a measurement target;
increasing the first flow rate of the first gas by a predetermined flow rate when a measurement value of the parameter meets a setting condition of the parameter; and
reducing the first flow rate of the first gas by the predetermined flow rate and fixing the reduced first flow rate when a measurement value of the parameter fails to meet the setting condition of the parameter after the first flow rate of the first gas has been increased by the predetermined flow rate.

11. The method of claim 9, wherein
the first flow rate of the first gas is set by:
inputting a measurement value of a parameter in an environment as a measurement target;
reducing the first flow rate of the first gas by a predetermined flow rate when a measurement value of the parameter does not meet a setting condition of the parameter; and
fixing the first flow rate of the first gas when a measurement value of the parameter turns out to meet the setting condition of the parameter after the first flow rate of the first gas has been reduced by the predetermined flow rate.

12. The method of claim 10, wherein
the first flow rate of the first gas is set by:
inputting a measurement value of a parameter in an environment as a measurement target;
reducing the first flow rate of the first gas by a predetermined flow rate when a measurement value of the parameter does not meet the setting condition of the parameter; and
fixing the first flow rate of the first gas when a measurement value of the parameter turns out to meet the setting condition of the parameter after the first flow rate of the first gas has been reduced by the predetermined flow rate.

\* \* \* \* \*